US006398756B2

(12) United States Patent
Peterson et al.

(10) Patent No.: US 6,398,756 B2
(45) Date of Patent: Jun. 4, 2002

(54) EMBOLIC PROTECTION SYSTEM AND METHOD INCLUDING AN EMBOLI-CAPTURING CATHETER

(75) Inventors: Charles R. Peterson, Murrieta; John A. Simpson, Carlsbad, both of CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/855,430

(22) Filed: May 14, 2001

Related U.S. Application Data

(63) Continuation of application No. 09/442,667, filed on Nov. 18, 1999, now abandoned.

(51) Int. Cl.[7] ............................................. A61M 29/00
(52) U.S. Cl. .................................................. 604/96.01
(58) Field of Search ............ 604/96.01, 101.01–101.05, 604/915–921, 6.09; 606/1, 191, 194, 159, 198, 200

(56) References Cited

U.S. PATENT DOCUMENTS

| | | | |
|---|---|---|---|
| 4,723,549 A | | 2/1988 | Wholey et al. |
| 4,794,928 A | * | 1/1989 | Kletschka ................... 128/344 |
| 4,997,435 A | | 3/1991 | Demeter |
| 5,100,425 A | | 3/1992 | Fischell et al. |
| 5,158,548 A | | 10/1992 | Lau et al. |
| 5,437,632 A | | 8/1995 | Engleson |
| 5,814,064 A | | 9/1998 | Daniel et al. |
| 5,827,324 A | | 10/1998 | Cassell et al. |
| 5,846,251 A | | 12/1998 | Hart |
| 5,911,734 A | | 6/1999 | Tsugita et al. |
| 5,980,555 A | * | 11/1999 | Barbut et al. ................ 606/200 |
| 5,989,281 A | | 11/1999 | Barbut et al. |

FOREIGN PATENT DOCUMENTS

| | | |
|---|---|---|
| WO | WO 98/39053 | 11/1998 |
| WO | WO 98/51237 | 11/1998 |

* cited by examiner

*Primary Examiner*—Manuel Mendez
(74) *Attorney, Agent, or Firm*—Fulwider Patton Lee & Utecht, LLP

(57) ABSTRACT

A system used in a blood vessel when an interventional procedure is being performed in a stenosed or occluded region to capture any embolic material which may be created and released into the bloodstream during the procedure. The system includes an emboli-capturing catheter which is capable of occluding a blood vessel distal to or at an interventional procedure site, perfusing the blood to enable blood to flow past the occlusion, and filtering the blood to capture embolic material which may be released into the blood during a therapeutic interventional procedure. The emboli-capturing catheter includes an expandable member which is capable of being expanded distal to or at the area of treatment at the interventional procedure site for occluding the blood vessel. The catheter further includes a plurality of perfusion inlet openings for enabling blood and emboli to pass therethrough, and an outlet opening or openings which, in cooperation with the filter media, are adapted to enable blood to pass therethrough while preventing emboli from passing therethrough. The catheter also includes filter media located in the distal end of the catheter or capable of being deployed outside and distal of the catheter for filtering the blood to capture any released embolic material.

29 Claims, 3 Drawing Sheets

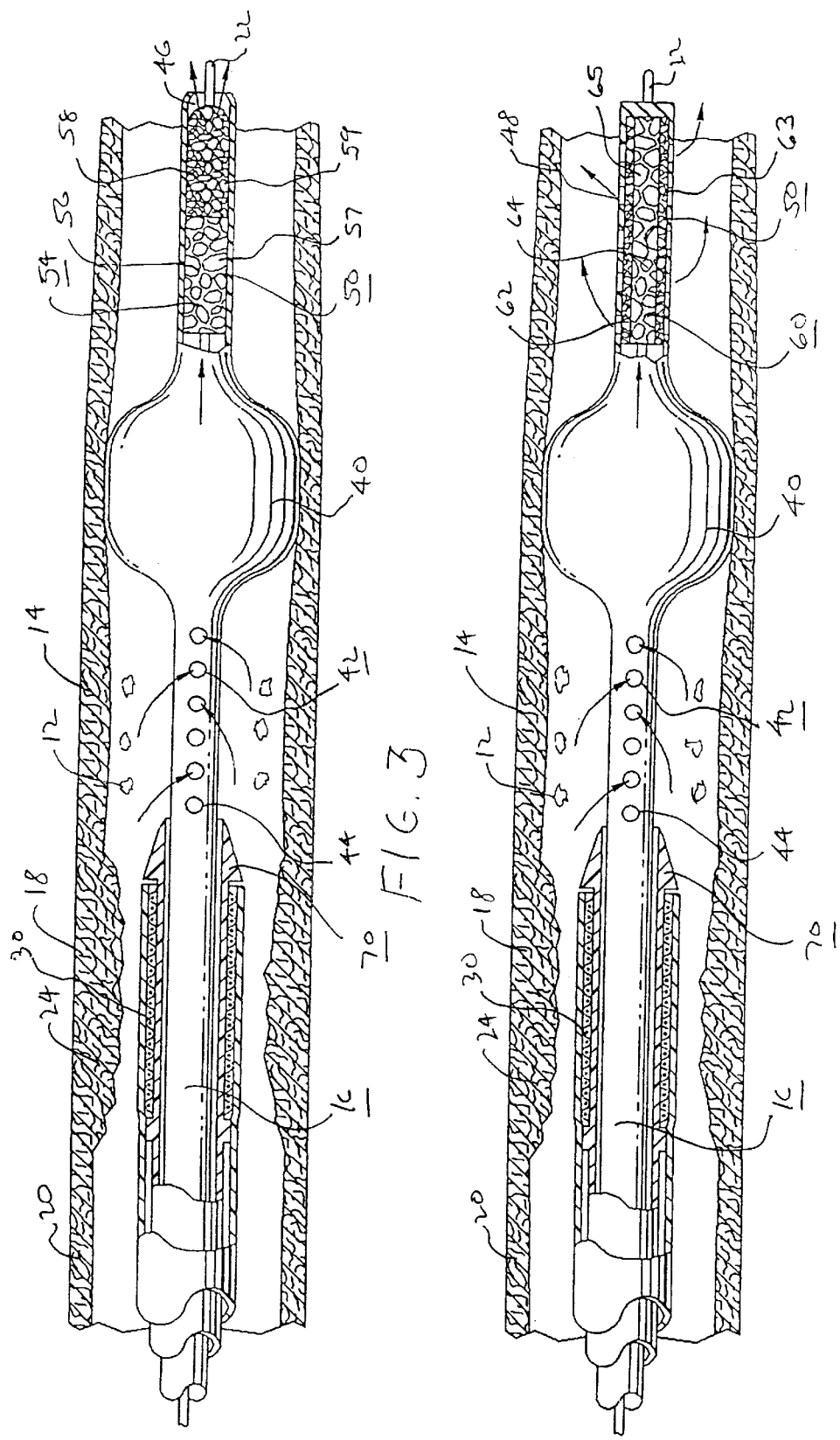

EMBOLIC PROTECTION SYSTEM AND METHOD INCLUDING AN EMBOLI-CAPTURING CATHETER

This application is a continuation of application Ser. No. 09/442,667, filed Nov. 18, 1999, now abandoned.

BACKGROUND OF THE INVENTION

The present invention relates generally to a system which can be used when an interventional procedure is being performed in a stenosed or occluded region of a blood vessel to capture any embolic material that may be created and released into the bloodstream during the procedure. The system of the present invention is particularly useful when performing balloon angioplasty, stenting procedures, laser angioplasty or atherectomy in critical vessels, such as the carotid arteries, where the release of embolic debris into the bloodstream can occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter is usually used to capture the shaved plaque or thrombus from the blood stream during this procedure.

In another widely practiced procedure, the stenosis can be treated by placing a device known as a stent into the stenosed region to hold open and sometimes expand the segment of blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and enter the bloodstream. Likewise, not all of the emboli created during an atherectomy procedure may be drawn into the vacuum catheter and, as a result, the remaining emboli may enter the bloodstream as well.

When any of the above-described procedures are performed in the cerebral arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature. Further techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the open end of the filter and enter the bloodstream as the filtering system is being collapsed for removal from the patient. In such a case, the act of collapsing the filter device may actually squeeze trapped embolic material through the opening of the filter. In other instances, the rate of blood percolating through the filtering material may be slower than the normal blood flow which can either cause the filtering material to tear or cause the filter to become displaced with the vessel due to the build up of fluid pressure behind the filter. Moreover, should the filter become clogged with debris, there is a possibility that blood circulation past the clogged filter will be insufficient for the downstream vessels and organs. If a filter should become clogged when in use in the carotid arteries, blood flow could be diminished to the vessels leading to the brain. While the brain may be capable of functioning for a short period of time without sufficient blood flow, blood stoppage of more than thirty to forty seconds could cause the patient to experience a seizure. If the physician administering the procedure is unaware that the filtering device is clogged and that there is little or no blood flowing to the brain, the injury to the patient can be as devastating as if an emboli itself had caused blockage of the cerebral arteries.

What has been needed is a reliable system and method for treating stenosis in blood vessels which prevent the risk of releasing embolic debris into the bloodstream that can cause blockage in vessels at downstream locations. The system and method should be capable of filtering any embolic debris which may be released into the bloodstream during the treatment, and yet allow a sufficient amount of oxygenated blood to flow past the filtering device to supply vital organs downstream from the treatment site. The system and method should be relatively easy for a physician to use and should provide a failsafe filtering system which removes all embolic debris from the bloodstream. Moreover, such a system should be relatively easy to deploy and remove from the patient's vasculature. The inventions disclosed herein satisfy all of these needs.

SUMMARY OF INVENTION

The present invention provides a system and method for capturing embolic debris in a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention occludes the blood vessel at a location distal to or at the area of treatment in the interventional procedure site, perfuses the blood to enable blood to flow past the occlusion, and filters the blood to capture any embolic debris which may be created during the interventional procedure.

In the present invention, the system includes an emboli-capturing catheter with an occlusion balloon to occlude a blood vessel, a plurality of perfusion openings to perfuse the blood past the occlusion, and filter media to capture embolic material. The emboli-capturing catheter of the present invention directs the blood flow through the area where the interventional procedure is to be performed and through the filter media located relative to the interventional site, which are designed to capture any friable plaque deposits. Additionally, the present invention allows blood to perfuse past the filter media to provide a continuous stream of blood to the organs located downstream.

In one particular embodiment of the present invention, the embolic protection system includes an emboli-capturing catheter which includes an elongated catheter body which has a proximal and distal end along with a main lumen which extends through the catheter body. An expandable member, such as an inflatable balloon, located near the distal end of the elongated catheter body, is in fluid communication with an inflation lumen. Upon inflation with a suitable fluid, the expandable member can be deployed within the blood vessel to prevent blood flow past the expandable member, for occluding the blood vessel at a location distal to the interventional procedure site. A plurality of perfusion openings in the elongated catheter body include inlet openings located proximal to the expandable member which extend into the main lumen, and an outlet opening or a plurality of outlet openings located at the distal end portion of the catheter body. As a result, even though the expandable member occludes the blood vessel, the blood will continue to flow into the catheter body through the perfusion inlet openings and through the perfusion lumen past the expandable member and out the perfusion outlet opening or openings. The blood flowing through the perfusion inlet openings and the catheter body lumen directs any embolic debris into the filter media positioned internally in the distal end portion of the catheter body and distal of the interventional site, for capturing embolic material which may be released into the blood in the blood vessel during the interventional procedure.

In another particular embodiment of the present invention, the embolic protection system includes an emboli-capturing catheter including an elongated catheter body having proximal and distal ends and a main lumen extending therethrough. The catheter further includes an expandable member, adapted to be inflated and deployed at the area of treatment to occlude the blood vessel and to prevent emboli from forming and being released from the area of treatment prior to deployment of filter media. The catheter also includes a plurality of perfusion openings for enabling the blood to continue to flow through the catheter body and out a distal end opening therein for perfusion of the blood. The catheter still further includes filter media adapted to be deployed externally of the catheter body for capturing embolic material which may be released into the bloodstream upon deflation of the expandable member and during the interventional procedure.

The elongated shaft of the emboli-capturing catheter, once deployed within the patient's vasculature, can be used as a guidewire to allow interventional instruments to be moved along the elongated shaft into the area of treatment in an over-the-wire arrangement. This eliminates the need to maintain a separate guidewire in the patient once the emboli-capturing catheter is in place.

Other features and advantages of the present invention will become more apparent from the following detailed description of the preferred embodiments of the invention, when taken in conjunction with the accompanying exemplary drawings.

BRIEF DESCRIPTION OF THE DRAWINGS

FIG. 2 is an elevational view, partially in section, similar to that shown in FIG. 1, in the first embodiment of the emboli-capturing catheter including a second mode of the filter media positioned therein.

FIG. 3 is an elevational view, partially in section similar to that shown in FIG. 1, in the first embodiment of the emboli-capturing catheter including a third mode of the filter media positioned therein.

DETAILED DESCRIPTION OF THE PREFERRED EMBODIMENTS

Figure 1:
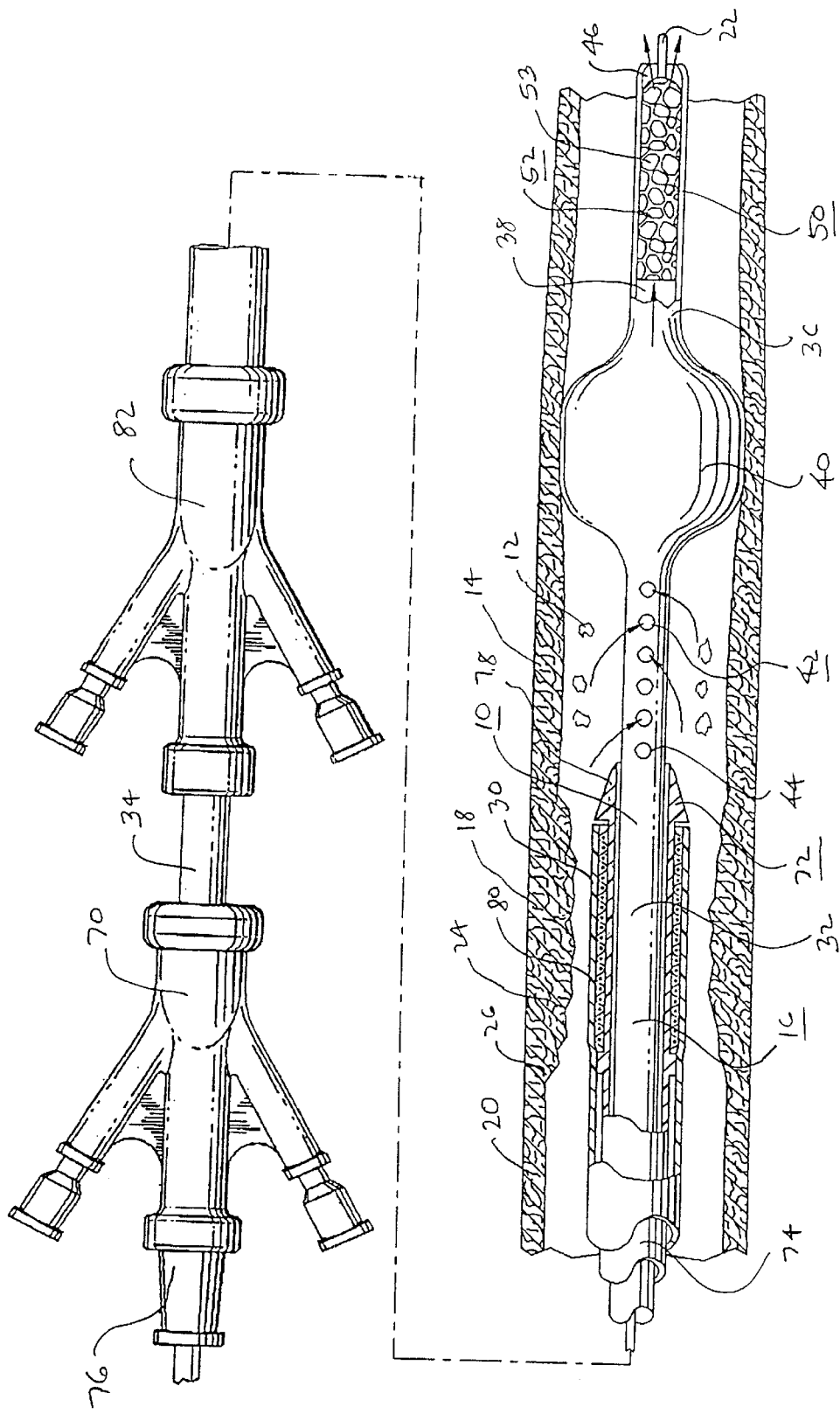
FIG. 1 is an elevational view, partially in section, depicting the embolic protection system of the present invention disposed within the internal carotid artery of the patient, in a first embodiment of the emboli-capturing catheter including a first mode of the filter media positioned therein for capturing embolic material.

The present invention is directed to an improved system and method for efficiently and effectively capturing embolic debris which may be released into the bloodstream when performing an interventional procedure in a blood vessel. The preferred embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Referring now to the drawings, wherein like reference numerals denote like or corresponding parts throughout the drawing figures, and particularly to FIGS. 1–4, an embolic protection system 10 is provided for capturing embolic material 12 which may be released into the blood in a blood vessel 14 during a therapeutic interventional procedure. The embolic protection system 10 comprises an emboli-capturing catheter 16. The emboli-capturing catheter 16 is adapted to occlude the blood vessel 14 at a location distal to or at an interventional procedure site in an area of treatment 18, to perfuse the blood to enable blood to flow past the occlusion, and to capture embolic material 12 which may be released into the blood in the blood vessel 14 during the interventional procedure. Additional details regarding the particular structure and shape of the various elements making up the emboli-capturing catheter 16 are provided below.

The embolic protection system 10 as shown in FIG. 1 may be placed within the carotid artery 20 or other blood vessel of the patient, and may be guided into position by a guide wire 22. The carotid artery 20 may have an area of treatment 18 wherein atherosclerotic plaque 24 has built up against the inside wall 26 which decreases the diameter of the carotid artery 20. As a result, blood flow may be diminished through this area. As will be discussed below, the therapeutic interventional procedure may comprise implanting a self-expanding stent 30 in the area of treatment 18, to compress the build-up of plaque 24 of the stenosis against the inside wall 26, to increase the diameter of the occluded area 18 of the artery 20, and to help restore sufficient flow of blood to the downstream vessels leading to the brain. The self-expanding stent 30 not only helps increase the diameter of the occluded area, but may help prevent restenosis in the area of treatment 18.

Figure 4:
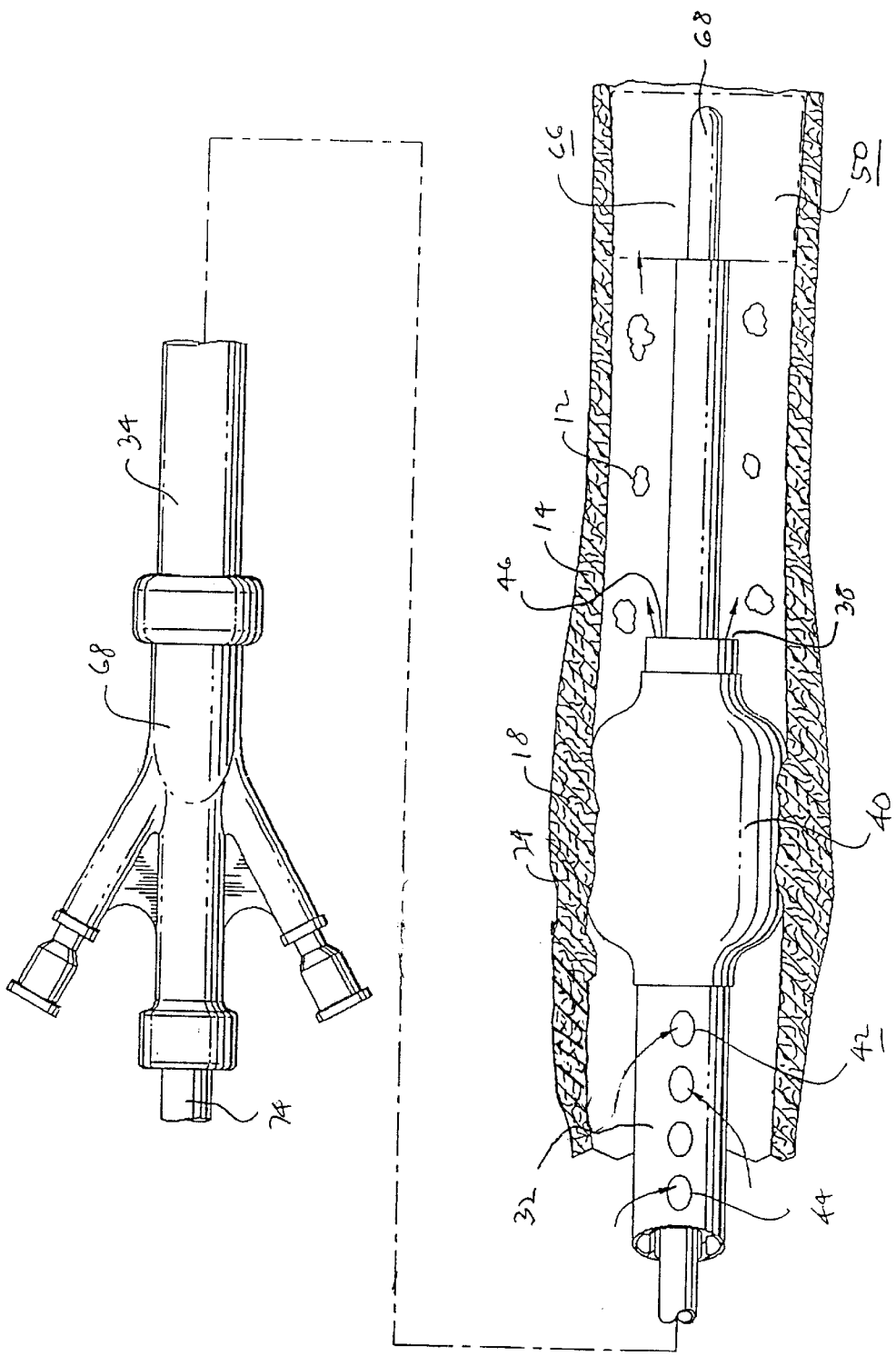
FIG. 4 is an elevational view, partially in section, of the embolic protection system of the present invention in a second embodiment of the emboli-capturing catheter including filter media deployed therefrom.

The emboli-capturing catheter 16 includes an elongated shaft 32 having a proximal end 34 and a distal end 36, and which has a central lumen 38 therein which may function as a perfusion lumen as described below. The emboli-capturing catheter 16 further includes an expandable member 40, which is shown in FIGS. 1–4 as an inflatable balloon, and which is located near a distal end 36 of the elongated shaft 32 of the emboli-capturing catheter 16. An inflation lumen (not shown) may also extend from the proximal end 34 to the distal end 36 of the elongated catheter shaft 32. The inflation lumen may receive and remove fluid, such as saline or other inflation fluid, for expanding and contracting the expandable member 40. As can be seen in FIGS. 1–3, the expandable member 40 may be deployed or expanded so as to make full contact with the walls 26 of the carotid artery 20 to occlude the blood vessel 14 and prevent the blood from flowing past the expandable member 40. As shown in FIG. 4, the expandable member 40 may be deployed or expanded at the treatment area 18 so as to make full contact with the plaque 24 in the walls 26 of the carotid artery 20 so as to occlude the blood vessel 14 to prevent blood from flowing past the expandable member 40, and to prevent emboli from forming and being released from the treatment area 18 prior to deployment of the filter media 50.

The elongated shaft 32 of the emboli-capturing catheter 16 further has a plurality of perfusion openings or ports 42 in the distal end 36 of the emboli-capturing catheter 16, to enable blood which is flowing through the blood vessel 14 and blocked by the expandable member 40, and embolic material 12 which may be released into the blood during the interventional procedure, to flow therethrough. The perfusion openings 42 include a plurality of inlet openings 44 located proximal of the expandable member 40, which communicate with the lumen 38 to allow blood and embolic material 12 to flow therethrough, and an outlet distal opening 46 adapted to enable blood to flow therethrough and, in cooperation with the filter media 50, to prevent embolic material 12 from passing therethrough. Alternatively, a plurality of outlet distal openings 48 may be positioned at circumferentially spaced-apart locations about the elongated shaft 32 proximate to the distal end 36.

The emboli-capturing catheter 16 also includes the filter media 50 located near the distal end 36 of the elongated shaft 32. The filter media 50 are adapted to be positioned at a location within the blood vessel 14 in a region distal to the treatment area 18, for passing blood therethrough and capturing embolic material 12 which may be released into the blood during the interventional procedure. As shown in the FIG. 1 embodiment of the invention, the filter media 50 may comprise mesh filter media 52, which include mesh filtering particles 53 therein, and which are adapted to be positioned within the distal end 36 of the elongated shaft 32 of the emboli-capturing catheter 16. As seen in FIG. 2, alternatively, filter media 54 may include a plurality of stages of filter material, including a first stage of coarse mesh filter media 56 including coarse mesh filtering particles 57 therein and a second stage of fine mesh filter media 58 including fine mesh filtering particles 59 therein, adapted to be positioned in the catheter 16 such that the second stage of fine mesh filter media 58 is distal to the first stage of coarse mesh filter media 56. As illustrated in FIG. 3, in another mode, filter media 60 includes fine mesh filter media 62, including fine mesh filtering particles 63 therein, adapted to be generally tubular in shape so as to extend about the inner wall of the distal end portion 36 of the central lumen 38, so as to cover the plurality of distal openings 48, and coarse mesh filter media 64, including coarse mesh filtering particles therein 65, about which the fine mesh filter media 62 is adapted to extend.

As shown in the embodiment in FIG. 4, alternatively, the filter media 50 may comprise filter media 66, represented in phantom in FIG. 4, which filter media 66 may comprise, for example, a net, a sponge, or the like, adapted to pass through the lumen 38 in collapsed form. The filter media 66 are comprised of material adapted to capture embolic material 12 while enabling blood to flow therethrough, such as a mesh fiber. The filter media 66 are adapted to be deployed externally of the elongated body 32 and outside the distal end 36 of the elongated shaft 32 of the emboli-capturing catheter 16. The filter media 66 may be mounted on a dowel 68 or similar element adapted to be extended through the distal opening 46 of the elongated shaft 32. The filter media 66 are adapted to be expandable upon projection thereof through the distal end 36 of the elongated shaft 32 of the emboli-capturing catheter 16, into the blood vessel 14 distal to the treatment area 18, so as to capture embolic material 12 therein. The filter media 66 are further adapted to be collapsible upon retraction thereof into the central lumen 36 in the elongated shaft 32 of the emboli-capturing catheter 16, along with the embolic material 12 captured therein.

As shown in FIG. 1, the emboli-capturing catheter 16 may further include a multi-arm adapter 70 attached to the proximal end 34 of the elongated shaft 32. The embolic protection system 10 may further comprise an interventional instrument catheter 72, adapted to be movable along the emboli-capturing catheter 16 so as to pass interventional instruments such as the self-expanding stent 30 to the interventional procedure site at the area of treatment 18. The interventional instrument catheter 72 includes an elongated shaft 74 which includes a proximal end 76 and a distal end 78 for delivering the interventional instruments (herein the stent 30 located near the distal end 78 of the elongated shaft 76) into the area of treatment 18. The interventional instrument catheter 72 may also include a retractable sheath 80 for covering the self-expanding stent 30 until it is positioned at the treatment area 18, and for being retracted so as to release the self-expanding stent 30 at the treatment area 18. The interventional instrument catheter 72 may further include a multi-arm adapter 82, such as a Tuohy-Borst adaptor, attached to a proximal end 76 of the elongated shaft 32.

In use, as illustrated in FIGS. 1–4, the embolic protection system 10 may be positioned in the patient's vasculature utilizing any one of a number of different methods. In one preferred method of positioning, the embolic-protection catheter 16 may be placed in the blood vessel 14 by utilizing the guidewire 22 which is inserted into the patient's vasculature and manipulated by the physician to the area of treatment 18. Thereafter, once the guidewire 22 is in place, the embolic-protection catheter 16 may be maneuvered over the guidewire 22 (via the central lumen 40) using well-known over-the-wire techniques to place the catheter 16 at a location proximal to the area of treatment 18. Once the catheter 16 is in place, the guidewire 22 may be removed from the central lumen 38 by the physician.

In the embodiment of FIGS. 1–3, as shown in FIG. 1, once the catheter 16 is in position in the blood vessel 14 with the expandable member 40 distal to the treatment area 18, the expandable member 40 of the catheter 16 may be inflated to occlude the blood vessel 14 and block the flow of blood entering into the treatment area 18. In the embodiment of FIG. 4 once the catheter 16 is in position in the blood vessel 14 with the expandable member 40 at the treatment area 18, the expandable member 40 of the catheter 16 may be inflated to occlude the blood vessel 14 and block the flow of blood entering into the treatment area 18. In both embodiments, the inflation of the expandable member 40 may be achieved at the proximal end 34 of the elongated shaft 32 utilizing the multi-arm adapter 70 which may be attached to an inflation pump or syringe to expand the expandable member 40.

Upon inflation of the expandable member 40, whereby the blood vessel 14 is occluded, the blood is forced to flow through the inlet openings 44 of the perfusion openings 42 into the central lumen 38. Blood flowing through the central lumen 38 flows through the filter media 50, and out of either the outlet distal opening 46 or the outlet distal openings 48 of the catheter 16, for perfusing the blood to enable blood to flow past the occlusion.

In the embodiment of the invention illustrated in FIGS. 1–3, as seen in FIG. 1, once the system 10 is placed in the patient's vasculature, with the expandable member 40 positioned distal to the treatment area 18, an interventional device, such as the interventional instrument catheter 72 including the a self-expanding stent 30, may be positioned in the area of treatment 18 utilizing the elongated shaft 32 of the emboli-capturing catheter 16 as a guidewire, again using well-known over-the-wire techniques. Upon positioning the self-expanding stent 30 at the treatment area 18, the retractable sheath 80 of the interventional instrument catheter 72 may be retracted through use of the adapter 82, releasing the self-expanding stent 30 to compress the build-up of plaque 24 in the treatment area. Any embolic material 12 which may be released into the blood during the therapeutic procedure may then be directed with the blood flow through the perfusion openings 42 and through the filter media 50 for filtering thereof, to capture embolic material 12 which may be released into the blood in the blood vessel 14 during the interventional procedure. The perfusion openings 42 are adapted to direct the embolic material 12 into the central lumen 40 and, in cooperation with the filter media 50, to prevent the embolic material 12 from passing therethrough with the blood for filtering the embolic material 12. The plurality of inlet openings 44 are adapted to enable embolic material 12 to pass therethrough into the central lumen 40. The outlet distal opening 46 in the embodiments of FIGS. 1 and 2, and the outlet distal openings 48 in the embodiment of FIG. 3, in conjunction with the filter media 50, are adapted to prevent large and small embolic material 12 from passing therethrough for filtering thereof.

The filter media 50 are adapted to capture and filter the emboli 12. The filter media 52 in the embodiment of FIG. 1 are adapted to capture and filter the large and small emboli 12. The filter media 54 in the embodiment of FIG. 2 are staged such that the large emboli 12 are captured and filtered by the coarse mesh filter media 56, and the small emboli 12 are captured and filtered by the fine mesh filter media 58. The filter media 60 in the embodiment of FIG. 3 are also adapted to capture and filter the large and small emboli 12. The coarse mesh filter media 64 filter the large emboli 12, and the fine mesh filter media 62, extending circumferentially about the coarse mesh filter media 64 and covering the plurality of outlet distal openings 48, are adapted to filter the small emboli 12. After the stent 30 is deployed in the treatment area 18, the interventional instrument catheter 70 may be withdrawn. Then, after a sufficient time passes to allow any embolic material 12 released into the blood to be captured by the filter media 50, the expandable member 40 may be deflated, and the embolic-capturing catheter 30 along the embolic material 12 captured in the filter media 50 may be withdrawn from the blood vessel 14, leaving the stent 30 in position therein.

In the embodiment of the invention illustrated in FIG. 4, once the system is in place in the patient's vasculature 14, the expandable member 40 may be used to contract and pin the plaque 24 at the treatment area 18, so as to occlude the blood vessel 14 and prevent emboli from forming and being released from the treatment area 18 prior to deploying the filter media 66. The filter media 66, which are adapted to pass through an enlarged lumen 38 in collapsed form, may then be deployed by projecting the filter media 66 through the distal end 36 of the elongated shaft 32 of the emboli-capturing catheter 16, into the blood vessel 14 distal to the treatment area 18, so as to capture embolic material 12 which may be released into the blood in the blood vessel 14. The expandable member 40 may then be deflated, with any embolic material released into the blood upon expansion and deflation of the expandable member 40 captured by the filter media 66. The self-expanding stent 30 may then be positioned and deployed, as set forth above. The deployed filter media 66 may then capture any further embolic material 12 released into the blood in the blood vessel 14 upon deployment of the stent 30. After the stent 30 is deployed in the treatment area 18, the interventional instrument catheter 72 may be withdrawn. Then, after a sufficient time to allow any further embolic material 12 released into the blood in the blood vessel 14 to be captured by the filter media 66, the filter media 66 may be retracted into the elongated shaft 32 of the emboli-capturing catheter 16 along with the embolic material 12 captured in the filter media 66, and the emboli-capturing catheter 30 may be withdrawn from the blood vessel 14, leaving the stent 30 in position therein. the filter media 66, and the emboli-capturing catheter 30 may be withdrawn from the blood vessel 14, leaving the stent 30 in position therein.

It should be appreciated that the particular embodiments of the filter media 50 are capable of being positioned in the blood vessel 14. However, other forms of filter media 50 may be utilized with the present invention without departing from the spirit and scope of the invention. For example, filter media 50 may further be comprised of other forms of material. Additionally, while the filter media 50 is shown as in various shapes in the embodiments herein, it can be formed in any one of a number of different shapes depending upon the construction desired.

The catheter assembly 16 of the present invention may be formed of conventional materials of construction. The catheter body 32 and the inflatable balloon 40 can be made out of relatively inelastic materials such as polyethylene, polyvinyl chloride, polyesters and composite materials. The various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the safety of performing interventional procedures by significantly reducing the risks associated with embolic material being created and released into the patient's bloodstream. Further modifications and improvements may additionally be made to the system and method disclosed herein without the departing from the scope of the invention. Accordingly, it is not intended that the invention be limited, except as by the appended claims.

What is claimed is:

1. A system for capturing embolic material which may be released into a blood vessel during therapeutic interventional procedure, comprising:

a catheter, adapted to oclude a blood vessel at a location distal to or at an interventional procedure site, to perfuse the blood to enable blood to flow past the occlusion, and to capture embolic material which may be released into the blood in the blood vessel during a therapeutic interventional procedure, including:

an elongated shaft, which includes proximal and distal ends, and which has a lumen therein, and a plurality of perfusion openings in the distal end portion thereof for perfusing the blood past the occlusion:

an expandable member, adapted to be located in the distal end portion of the elongated shaft and to be expandable within the blood vessel at a location distal to or at the interventional procedure site so as to occlude the blood vessel; and filter media, adapted to be located in the distal end protion of the elongated shaft distal of the expandable member and to be positionable within the blood vessel distal to the interventional procedure site, for passing blood therethrough and capturing embolic material which may be released into the blood in the blood vessel during the interventional prooocedure.

2. The system of claim 1, wherein the catheter includes an inflation lumen in fluid communication with the expandable member adapted to inflate the expandable member outwardly upon receipt of fluid through the inflation lumen and to collapse the expandable member inwardly towards the elongated shaft upon evacuation from the inflation lumen.

3. The system of claim 1, wherein the plurality of perfusion openings include a plurality of inlet openings located proximal of the expandable member, which communicate with the lumen, for perfusion of the blood, to enable blood which is flowing through the blood vessel and blocked by the expandable member, and embolic material which may be released into the blood during the interventional procedure, to flow therethrough, and an outlet opening located distal to the expandable member, which communicates with the main lumen, for perfusion of the blood, to enable blood which flows through the filter media to flow into and through the blood vessel.

4. The system of claim 1, wherein the lumen comprises a perfusion lumen which permits blood flow past and through the filter media.

5. The system of claim 1, further comprising a guide wire for guiding movement of the emboli-capturing catheter.

6. The system of claim 1, further comprising an interventional instrument catheter adapted to be moveable along the emboli-capturing catheter so as to pass interventional instruments to the interventional procedure site.

7. The system of claim 3, wherein the outlet opening comprises a plurality of outlet openings positioned at circumferentially spaced-apart locations about the catheter shaft proximate to the distal end of the catheter shaft.

8. The system of claim 3, wherein the plurality of inlet openings are adapted to enable emboli to pass therethrough.

9. The system of claim 3, wherein the outlet opening is adapted to prevent emboli from passing therethrough.

10. A system for capturing embolic material which may be released into a blood vessel during a therapeutic interventional procedure, comprising:

a catheter, adapted to occlude a blood vessel at a location distal to an interventional procedure site, to perfuse the blood to enable blood to flow past the occlusion, and to capture embolic material which may be released into the blood in the blood vessel during a therapeutic interventional procedure, including:

an elongated shaft, which includes proximal and distal ends, and which has a lumen therein, and a plurality of perfusion openings in the distal end portion thereof for perfusing the blood past the occlusion:

an expandable member, adapted to be located in the distal end portion of the elongated shaft and to be expandable within the blood vessel at a location distal to the interventional procedure site so as to occlude the blood vessel; and filter media, adapted to be located in the distal end portion of the elongated shaft distal of the expandable member and to be positionable within the blood vessel distal to the interventional procedure site, for passing blood therethrough and capturing embolic material which may be released into the blood in the blood vessel during the interventional procedure.

11. The system of claim 10, wherein the plurality of perfusion openings include a plurality of inlet openings located proximal of the expandable member, which communicate with the lumen, for perfusion of the blood, to enable blood which is flowing through the blood vessel and blocked by the expandable member, and embolic material which may be released into the blood during the interventional procedure, to flow therethrough, and an outlet opening located distal to the expandable member, which communicates with the main lumen, for perfusion of the blood, to enable blood which flows through the filter media to flow into and through the blood vessel.

12. The system of claim 10, wherein the filter media include coarse mesh filter particles and fine mesh filter particles.

13. The system of claim 10, wherein the filter media comprise a plurality of stages of filter particles.

14. The system of claim 11, wherein the outlet opening comprises a plurality of outlet openings positioned at circumferentially spaced-apart locations about the catheter shaft proximate to the distal end of the catheter shaft.

15. The system of claim 12, wherein the fine mesh filter particles are adapted to be positioned proximate to the outlet opening.

16. The system of claim 12, wherein the plurality of stages of the filter material comprise a first stage of coarse mesh filter particles, and a second stage of fine mesh filter particles, adapted to be positioned in the catheter such that the second stage is distal to the first stage.

17. The system of claim 14, wherein the filter media include fine mesh filter particles, and the fine mesh filter particles are adapted to be shaped so as to extend about the inner wall of the distal end portion of the lumen so as to cover the plurality of outlet openings.

18. The system of claim 15, wherein the coarse mesh filter particles are adapted to be positioned proximal of the fine mesh filter particles.

19. The system of claim 17, wherein the shape of the filter media comprises a generally tubular shape.

20. A method of capturing embolic material released into a blood vessel during a therapeutic interventional procedure, in a system which comprises a catheter, adapted to occlude a blood vessel at a location distal to or at an interventional procedure side, to perfuse the blood to enable blood to flow past the occlusion, and to capture embolic material which may be released into the blood in the blood vessel during a therapeutic interventional procedure, including an elongated shaft, which includes proximal and distal ends, and which has a lumen therein, and a plurality of perfusion openings in the distal end portion thereof for perfusing the blood past the occlusion, an expandable member, adapted to be located in the distal end portion of the elongated shaft and to be expandable within the blood vessel at a location distal to or at the interventional procedure site so as to occlude the blood vessel, and filter media, adapted to be located in the distal end portion of the elongated shaft distal of the expandable member and to be positionable within the blood vessel distal to the interventional procedure site, for passing blood therethrough and capturing embolic material which may be released into the blood in the blood vessel during the interventional procedure, wherein the method comprises:

positioning the catheter in the interventional procedure site such that the expandable member and the filter media are located within the blood vessel in the region at a location distal to or at the interventional procedure site;

expanding the expandable member within the blood vessel at the location distal to or at the interventional procedure site so as to occlude the blood vessel;

perfusing the blood through the catheter;

performing the interventional procedure, which may release embolic material into the blood; and filtering the blood through the filter media so as to capture embolic material which may be released into the blood upon performing the interventional procedure.

21. The method of claim 20, wherein the catheter includes an inflation lumen in fluid communication with the expandable member, adapted to inflate the expandable member outwardly upon receipt of fluid through the inflation lumen and to collapse the expandable member inwardly towards the elongated shaft upon evacuation of fluid from the inflation lumen, and wherein expanding the expanding member further comprises pumping the fluid through the inflation lumen to inflate the expandable member.

22. The method of claim 20, wherein the plurality of perfusion openings include a plurality of inlet openings located proximal of the expandable member, which communicate with the lumen, for perfusion of the blood, to enable blood which is flowing through the blood vessel and blocked by the expandable member, and embolic material which may be released into the blood during the interventional procedure, to flow therethrough, and an outlet opening located distal to the expandable member, which communicates with the main lumen, for perfusion of the blood, to enable blood which flows through the filter media to flow into and through the blood vessel, wherein perfusing further comprises perfusing the blood and the embolic material which may be released into the blood through the plurality of inlet openings and the filter media, and perfusing the blood through the outlet opening into the blood vessel.

23. The method of claim 20, wherein the lumen comprises a perfusion lumen which permits blood flow past the positioned filtering member, further comprising perfusing the blood and the embolic material which may be released into the blood through the perfusion lumen and past the filter media.

24. The method of claim 20, further comprising a guide wire for guiding movement of the emboli-capturing catheter, further comprising guiding movement of the emboli-capturing catheter along the guide wire.

25. The method of claim 20, further comprising an interventional instrument catheter for passing interventional instruments along the emboli-capturing catheter to the interventional procedure site, further comprising passing the interventional instrument catheter along the embolic-capturing catheter to the interventional procedure site.

26. A method of capturing embolic material released into a blood vessel during a therapeutic interventional procedure, in a system which comprises a catheter, adapted to occlude a blood vessel at a location distal to an interventional procedure side, to perfuse the blood to enable blood to flow past the occlusion, and to capture embolic material which may be released into the blood in the blood vessel during a therapeutic interventional procedure, including an elongated shaft, which includes proximal and distal ends, and which has a lumen therein, and a plurality of perfusion openings in the distal end portion thereof for perfusing the blood past the occlusion, an expandable member, adapted to be located in the distal end portion of the elongated shaft and to be expandable within the blood vessel at a location distal to the interventional procedure site so as to occlude the blood vessel, and filter media, adapted to be located in the distal end portion of the elongated shaft distal of the expandable member and to be positionable within the blood vessel distal to the interventional procedure site, for passing blood therethrough and capturing embolic material which may be released into the blood in the blood vessel during the interventional procedure, wherein the method comprises:

positioning the catheter in the interventional procedure site such that the expandable member and the filter media are located within the blood vessel in the region at a location distal to the interventional procedure site;

expanding the expandable member within the blood vessel at the location distal to the interventional procedure site so as to occlude the blood vessel;

perfusing the blood through the catheter;

performing the interventional procedure, which may release embolic material into the blood; and filtering the blood through the filter media so as to capture embolic material which may be released into the blood upon performing the interventional procedure.

27. The method of claim 26, wherein the plurality of perfusion openings include a plurality of inlet openings located proximal of the expandable member, which communicate with the lumen, for perfusion of the blood, to enable blood which is flowing through the blood vessel and blocked by the expandable member, and embolic material which may be released into the blood during the interventional procedure, to flow therethrough, and an outlet opening located distal to the expandable member, which communicates with the main lumen, for perfusion of the blood, to enable blood which flows through the filter media to flow into and through the blood vessel, wherein perfusing further comprises perfusing the blood and the embolic material which may be released into the blood through the plurality of inlet opening and the filter media, and perfusing the blood through the outlet opening into the blood vessel.

28. The method of claim 26, wherein the filter media include coarse mesh filter media and fine mesh filter media, and wherein filtering further comprises filtering the blood through the coarse mesh filter media and the fine mesh filter media.

29. The system of claim 26, wherein the filter media comprise a plurality of stages of filter material, and wherein filtering further comprises filtering the blood through the plurality of stages of the filter material.

* * * * *